United States Patent
Shetty

(10) Patent No.: US 11,612,769 B2
(45) Date of Patent: Mar. 28, 2023

(54) ORAL HEALTH CARE FORMULATION AND METHOD OF PREPARATION THEREOF

(71) Applicant: Muniyal Ayurvedic Research Centre, Manipal (IN)

(72) Inventor: M Vijayabhanu Shetty, Karnataka (IN)

(73) Assignee: MUNIYAL AYURVEDIC RESEARCH CENTRE, Manipal (IN)

( * ) Notice: Subject to any disclaimer, the term of this patent is extended or adjusted under 35 U.S.C. 154(b) by 102 days.

(21) Appl. No.: 16/130,391

(22) Filed: Sep. 13, 2018

(65) Prior Publication Data
US 2019/0009112 A1   Jan. 10, 2019

Related U.S. Application Data

(60) Provisional application No. 62/558,674, filed on Sep. 14, 2017.

(51) Int. Cl.
| | | |
|---|---|---|
| A61Q 11/00 | (2006.01) | |
| A61K 36/185 | (2006.01) | |
| A61K 9/20 | (2006.01) | |
| A61K 36/48 | (2006.01) | |
| A61K 36/736 | (2006.01) | |
| A61K 36/29 | (2006.01) | |
| A61K 36/484 | (2006.01) | |
| A61K 8/19 | (2006.01) | |

(Continued)

(52) U.S. Cl.
CPC ............ *A61Q 11/00* (2013.01); *A61K 8/19* (2013.01); *A61K 8/9789* (2017.08); *A61K 9/20* (2013.01); *A61K 33/26* (2013.01); *A61K 36/185* (2013.01); *A61K 36/29* (2013.01); *A61K 36/48* (2013.01); *A61K 36/484* (2013.01); *A61K 36/736* (2013.01)

(58) Field of Classification Search
CPC ...... A61Q 11/00; A61K 36/48; A61K 36/736; A61K 36/29; A61K 36/484; A61K 8/19; A61K 8/9789; A61K 33/26; A61K 36/185; A61K 9/20
See application file for complete search history.

(56) References Cited

U.S. PATENT DOCUMENTS 3,615,339 A * 10/1971 Stone ................... B22F 9/20
75/347
6,866,840 B2 * 3/2005 Yano .................. A61K 8/25
424/49

(Continued)

OTHER PUBLICATIONS

Ajagannanavar et al., "Effect of Aqueous and Alcoholic Licorice (*Glycyrrhiza glabra*) Root Extract Against *Streptococcus mutans* and Lactobacillus Acidophilus in Comparison to Chlorhexidine: An In Vitro Study" Journal of International Oral Health 2014; 6(4):29-34 (Year: 2014).*

(Continued)

*Primary Examiner* — Gollamudi S Kishore
(74) *Attorney, Agent, or Firm* — Pilloff Passino & Cosenza LLP; Sean A. Passino; Rachel K. Pilloff

(57) ABSTRACT

Oral health care formulation and method of preparation for the same are disclosed herein. The disclosed oral care composition includes a combination of various herbs and minerals, and may be used to maintain good oral hygiene. Further, a method of oral health care is also disclosed in the various embodiments herein.

20 Claims, 4 Drawing Sheets

(51) Int. Cl.
    *A61K 8/9789*     (2017.01)
    *A61K 33/26*     (2006.01)

(56) References Cited

U.S. PATENT DOCUMENTS

| | | | | |
|---|---|---|---|---|
| 7,736,629 B2* | 6/2010 | Kamath | ................. | A61Q 11/00 |
| | | | | 424/58 |
| 2007/0098649 A1* | 5/2007 | Wu | ....................... | A61K 45/06 |
| | | | | 424/49 |
| 2010/0303737 A1* | 12/2010 | Hurtig | ..................... | A61K 8/26 |
| | | | | 424/48 |

OTHER PUBLICATIONS

Sharma, "In vitro antibacterial activity of certain folk medicinal plants from Darjeeling Himalayas used to treat microbial infections", Journal of Pharmacognosy and Phytochemistry 2013; 2 (4): 1-4 (Year: 2013).*

Government of India, the Biological Diversity Act, 2002.†

\* cited by examiner
† cited by third party

ORAL HEALTH CARE FORMULATION AND METHOD OF PREPARATION THEREOF

CROSS REFERENCE TO RELATED APPLICATION

This application is based on and derives the benefit of U.S. Provisional Application 62/558,674 filed on Sep. 14, 2017 the contents of which are incorporated herein by reference in their entirety.

TECHNICAL FIELD

The embodiments disclosed in this specification relate to herbo-mineral composition effective in oral health care, particularly in the treatment and prevention of conditions relating to oral cavity. It also relates to the process of preparation of such composition.

BACKGROUND

Healthy teeth and gums are a result of good oral care. Oral care compositions such as toothpastes, toothpowders, mouthwash, etc are used in order to ensure that the oral cavity is devoid of oral infections. The commonly known oral problems such as gingivitis, dental caries, plaques, tartar, bad breath and sensitive teeth can be avoided by maintaining good oral hygiene.

The use of dentifrice in maintaining good oral hygiene has long been known. Dentifrices having triclosan, stannous, zinc, sodium, fluoride etc. are well known and used to combat oral problems. However, these are potentially harmful ingredients, and their extensive use may do irreversible damage to health. Hence, the use of natural herbal products may be more preferable.

Alternatively, nature friendly practices in maintaining good oral health are known. The knowledge of using Neem twigs for brushing teeth is ancient in India. The chewing of cloves after every meal in order to maintain fresh breath and strengthen gums is an age-old practice. One of the recommendations in Ayurveda for alleviating toothache is the use of ginger and rock salt for immediate relief.

In the backdrop of the rich traditional knowledge pertaining to Oral health available in literature, various attempts in achieving efficient oral care compositions have been made. Extracts of traditionally known herbs such as neem, tulsi, ginger, acacia, cloves, etc. are frequently used in Oral care products and compositions. However, achieving a stable and effective dentifrice having natural ingredients can be challenging. There exists a need for an effective method of maintaining good oral hygiene.

Objects of the Disclosed Embodiments

The principal object of the embodiments disclosed herein is to provide a composition and method of Oral health care.

A second object of the embodiments disclosed herein is to provide a composition and method for treatment of conditions associated with Oral cavity.

Another object of the embodiments disclosed herein is to provide a composition and method for prevention of conditions associated with Oral cavity.

Another object of the embodiments disclosed herein is to provide a herbo-mineral composition used to improve oral health and a method for its preparation.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated by way of example in the accompanying drawings. The embodiments herein will be better understood from the following description with reference to the drawings, in which.

DETAILED DESCRIPTION

Figure 1A:
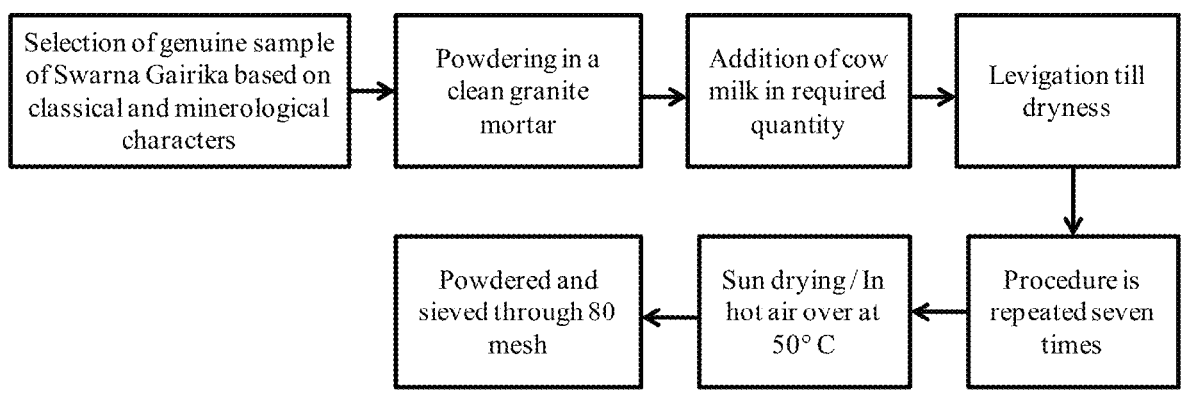
FIG. 1(a) depicts a flowchart for the purification and potentiation of Hematite (Swarna gairika Shodhana)

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve an oral care composition and a method of its preparation. Disclosed embodiments also include a method of treatment and prevention of conditions associated with oral cavity. In various embodiments herein, conditions associated with oral cavity would include any condition arising from poor oral care practices. The conditions associated with oral cavity would include undesirable oral problems such as oral infections, oral malodor, plaque, gingivitis, periodontal diseases, teeth discoloration, teeth sensitivity, etc. Accordingly, embodiments of a method of oral health care by using the disclosed oral care composition is provided herein.

Composition

The disclosed embodiments herein provide oral care composition having a combination of selected herbs and minerals. In an embodiment, the oral care composition includes herb element and mineral element. In another embodiment, the herbal composition includes herb element, mineral element and at least one salt. In yet another embodiment, the oral care composition may further include Lac from *Laccifer lacca*. In another embodiment, the oral care composition may further include one or more suitable excipient.

Herb Element

In an embodiment, the herb element includes the herbs *Prunus cerasoides*, *Glycyrrhiza glabra*, *Berberis aristata*, *Acacia catechu* and *Acacia arabica* or their extracts, or the active ingredients extracted from these herbs.

In another embodiment, the herb element further includes at least one of the herbs selected from *Santalum album*, *Vetiveria zizanioides*, *Rubia cordifolia*, *Woodfordia fruticosa*, *Cyperus rotundus*, *Cinnamomum zeylanicum*, *Elettaria cardamomum*, *Messua ferrea*, *Nardostachys jatamansi*, *Symplocos racemosus*, *Curcuma longa*, *Mimosa pudica*, *Acorus calamus*, *Aquilaria agallocha*, *Syzygium aromaticum*, *Piper cubeba*, *Emblica officinalis*, *Terminalia chebula*, *Terminalia bellerica*, *Ficus benghalensis*, *Ficus glomerata*, *Psoralea corylifolia*, *Jasminum officinale* and *Cinnamomum camphor* or their extracts, or the active ingredients extracted from these herbs.

The herb element may include a specific part of the herb (also referred as herb component) such as roots, flowers, seeds, fruits, stem, bark, resin, rhizome, whole plant, extract etc. In an embodiment, the herb element may include heartwood of *Santalum album*, *Prunus cerasoides* and *Aquilaria agallocha*; root of *Vetiveria zizanioides*, *Rubia cordifolia*, *Cyperus rotundus*, *Glycyrrhiza glabra*, *Nardostachys jatamansi* and *Acorus calamus*; flowers of *Woodfordia fruticosa*; flower bud of *Syzygium aromaticum*; stamen of *Messua ferrea*; bark of *Cinnamomum zeylanicum*, *Symplocos racemosus*, *Acacia arabica*, *Ficus benghalensis* and *Ficus glomerata*; seeds of *Elettaria cardamomum* and *Psoralea corylifolia*; rhizome of *Curcuma longa*, root of *Berberis aristata*; plant of *Mimosa pudica*; fruit of *Piper cubeba*, *Emblica officinalis*, *Terminalia chebula* and *Terminalia bellerica*; leaves of *Jasminum officinale*; Karpura (sublimate) of *Cinnamomum camphor*; and heartwood of *Acacia catechu*, or their extracts. However, it is also within the scope of invention for the herbal composition to include other herb components such as leaf, flowers, etc. without otherwise deterring intended function of the composition.

The herb element may also include any form of secretion, resin or discharge that may be exuded by the herb or any part of the herb. However, it is also within the scope of the claims provided herein for the herbo-mineral composition to include other herb components such as leaf, flowers, etc. without otherwise deterring intended function of the herbo-mineral composition.

The herb component of the herbs, disclosed herein, maybe included in the composition in any form that is generally known in the field. For example, the herb component may be included as fresh or maybe processed to form extracts, dried, powdered, sublimated, pelleted, concentrated, etc. In an embodiment, the herb components are dried and powdered which is further incorporated into the composition. In another embodiment, the heartwood of *Acacia catechu* is included in the form of water extract (also referred to as Khadirasara). In yet another embodiment, the root of *Berberis aristata* is included in the form of extract (also referred to as Rasanjana). Further, in an embodiment, the herb component is a sublimate (Karpura) of *Cinnamomum camphor*.

In an embodiment, the herb element includes *Glycyrrhiza glabra* in an amount ranging from 6 to 10 wt %, *Berberis aristata* in an amount ranging from 6 to 10 wt %, *Acacia catechu* in an amount ranging from 6 to 10 wt %, *Acacia arabica* in an amount ranging from 6 to 10 wt % and *Prunus cerasoides* in an amount ranging from 2 to 6 wt %. Further, in another embodiment, the herb element includes at least one of *Santalum album*, *Vetiveria zizanioides*, *Rubia cordifolia*, *Woodfordia fruticosa*, *Cyperus rotundus*, *Cinnamomum zeylanicum*, *Elettaria cardamomum*, *Messua ferrea*, *Nardostachys jatamansi*, *Symplocos racemosus*, *Curcuma longa*, *Mimosa pudica*, *Acorus calamus*, *Aquilaria agallocha*, *Syzygium aromaticum*, *Piper cubeba*, *Emblica officinalis*, *Terminalia chebula*, *Terminalia bellerica*, *Ficus benghalensis*, *Ficus glomerata*, *Psoralea corylifolia*, *Jasminum officinale* and *Cinnamomum camphor* in an amount of ≤3 wt % each.

Mineral Element

In an embodiment, the mineral element may include Ores or Bhasmas (calcined preparations). In an embodiment, the mineral element includes Hematite (Red ochre or Swarna gairika). However, it is also within the scope of claims provided herewith for the herbo-mineral composition to include, as a substitute or additionally, other similar ores or calcined preparations or minerals without otherwise deterring from the intended function of the herbo-mineral composition.

In an embodiment, the mineral element includes Hematite (Red ochre or Swarna gairika) in an amount of ≤3 wt %.

Salt

In an embodiment, the salt includes Rock salt. In an embodiment, the herbo-mineral composition disclosed herein includes rock salt in an amount of ≤3 wt %. However, it is also within the scope of claims provided herewith for the herbo-mineral composition to include, as a substitute or additionally, other similar salts without otherwise deterring from the intended function of the herbo-mineral composition.

In another embodiment, the oral care composition may further include Laksha resin from *Laccifer lacca*. In an embodiment, the herbo-mineral composition disclosed herein includes Laksha resin in an amount of ≤3 wt %.

The disclosed composition, in the various embodiments herein, may further include one or more suitable excipients. The suitable excipients include solvents, binders, lubricants, herbal carriers, oils and salts that are generally known in the art. In a preferred embodiment, the excipient includes gum acacia.

Further, the amount of herb element and mineral element that may be included in the various embodiments of the disclosed composition may be in the range of 0 to 10 wt %. In an embodiment, the composition includes *Glycyrrhiza glabra* (6 to 10 wt %), *Berberis aristata* (6 to 10 wt %), *Acacia catechu* (6 to 10 wt %), *Acacia arabica* (6 to 10 wt %), *Prunus cerasoides* (2 to 6 wt %) and Hematite (≤3 wt %).

In an embodiment, the composition includes *Glycyrrhiza glabra* (6 to 10 wt %), *Berberis aristata* (6 to 10 wt %), *Acacia catechu* (6 to 10 wt %), *Acacia arabica* (6 to 10 wt %), *Prunus cerasoides* (2 to 6 wt %), Hematite (≤3 wt %) and Laksha resin (≤3 wt %).

In another embodiment, the composition includes *Glycyrrhiza glabra* (6 to 10 wt %), *Berberis aristata* (6 to 10 wt %), *Acacia catechu* (6 to 10 wt %), *Acacia arabica* (6 to 10 wt %), *Prunus cerasoides* (2 to 6 wt %), Hematite (≤3 wt %) and rock salt (≤3 wt %).

Further, in an embodiment, the composition further includes at least one of *Santalum album*, *Vetiveria zizanioides*, *Rubia cordifolia*, *Woodfordia fruticosa*, *Cyperus rotundus*, *Cinnamomum zeylanicum*, *Elettaria cardamomum*, *Messua ferrea*, *Nardostachys jatamansi*, *Symplocos racemosus*, *Curcuma longa*, *Mimosa pudica*, *Acorus calamus*, *Aquilaria agallocha*, *Syzygium aromaticum*, *Piper cubeba*, *Emblica officinalis*, *Terminalia chebula*, *Terminalia bellerica*, *Ficus benghalensis*, *Ficus glomerata*, *Psoralea*

*corylifolia, Jasminum officinale* and *Cinnamomum camphor* in an amount in the range of ≤2 wt %.

Further, the amount of gum acacia may be any amount suitable to perform the activity of an excipient. In an embodiment, the composition may include gum acacia in the range of 0 to 50 mg per 500 mg of the composition, preferably 10 wt %.

However, it is apparent that slight variations in the amount of the ingredients may be performed without otherwise deterring from the intended function of the herbo-mineral composition.

The herbo-mineral composition disclosed herein may be formulated in various dosage forms such that it is suitable for oral cavity. The herbo-mineral composition may be in the form of tablets, pastes, gels, powder, mouth sprays, pellets, lozenges, granules, solutions, emulsions, suspensions, or any other form suitable for use. In an embodiment, the herbo-mineral composition is formulated in the form of tablets, preferably 500 mg tablets. For example: Table 1A depicts the quantities of each ingredient in a 500 mg tablet.

Further disclosed herein, is a tablet for treating/preventing/managing Renal disorders. In an embodiment, the tablet is a 500 mg tablet having herb element, mineral element and an excipient as depicted in Table 1A.

art that many modifications, both to materials and methods, may be practiced without departing from the scope of the present invention.

TABLE 2

| Test Parameters | Standard Specifications |
| --- | --- |
| Description | Brown biconvex shaped tablets |
| Identification | Positive for iron, calcium and tannins |
| Average weight | 500 mg ± 12.5 mg |
| Uniformity of weight | ±2.5% of actual average weight |
| Average tablet hardness | 1.5-2.0 kg/cm$^2$ |
| Loss on drying | 3-4% w/w |
| Methanol soluble extractive | 25-30% w/v |
| Chloroform soluble extractive | 7-8% w/v |
| Ash value | 18-20% w/w |
| Average Disintegration time | 10-12 minutes |
| ASSAY | Each tablet contains: Iron - 1.2-2.0 mg, Calcium - 7-8 mg |

Method

Disclosed herein are embodiments of a method of preparing the herbo-mineral composition. In an embodiment, the method includes,

TABLE 1A

Each 500 mg tablet includes:

| S. NO. | SANSKRIT NAME | SCIENTIFIC NAME | QUANTITY |
| --- | --- | --- | --- |
| 1 | Candan dry heartwood | *Santalum album* | 10 mg |
| 2 | Padmaka dry heartwood | *Prunus cerasoides* | 20 mg |
| 3 | Usheera dry root | *Vetiveria zizanoides* | 10 mg |
| 4 | Manjishtha dry root | *Rubia cordifolia* | 10 mg |
| 5 | Dhataki dry flowers | *Woodfordia fruticosa* | 10 mg |
| 6 | Musta dry root | *Cyperus rotundus* | 10 mg |
| 7 | Yashti dry root | *Glycyrrhiza glabra* | 40 mg |
| 8 | Tvak dry bark | *Cinnamomum zeylanicum* | 10 mg |
| 9 | Ela dry seeds | *Elettaria cardamomum* | 10 mg |
| 10 | Nagakeshara dry stamens | *Messua ferrea* | 10 mg |
| 11 | Laksha resin | *Lac* (produced by *laccifera lacca*) | 10 mg |
| 12 | Jataamsi dry rot | *Nardostachys jatamamsi* | 10 mg |
| 13 | Lodhra dry bark | *Symplocas racemosus* | 10 mg |
| 14 | Haridra dry rhizome | *Curucma longa* | 10 mg |
| 15 | Rasanjana - extract of root | *Berberis aristata* | 40 mg |
| 16 | Lajjalu dry plant | *Mimosa pudica* | 10 mg |
| 17 | Vacha dry root | *Acorus calamus* | 10 mg |
| 18 | Agaru dry heartwood | *Aquilaria agallocha* | 10 mg |
| 19 | Lavanga dry flower bud | *Syzygum aromaticum* | 10 mg |
| 20 | Kankola dried fruit | *Piper cubeba* | 10 mg |
| 21 | Amalaki dry fruits | *Emblica officinalis* | 10 mg |
| 22 | Hareetaki dry fruits | *Terminalia chebula* | 10 mg |
| 23 | Vibhitaki dry fruits | *Terminalia bellerica* | 10 mg |
| 24 | Khadira Sara - water extract of heartwood | *Acacia catechu* | 40 mg |
| 25 | Babbula dry bark | *Acacia arabica* | 40 mg |
| 26 | Vata dry bark | *Ficus bengalensis* | 10 mg |
| 27 | Udumbara dry bark | *Ficus glomerata* | 10 mg |
| 28 | Bakuchi dry seeds | *Psoralia corylifolia* | 10 mg |
| 29 | Jati dry leaves | *Jasminum officinale* | 10 mg |
| 30 | Karpura - sublimate | *Cinnamomum camphor* | 10 mg |
| 31 | Gairika ore | Red ochre (haematite) | 10 mg |
| 32 | Saindhava salt | Rock salt | 10 mg |
| 33 | Gum acacia | *Acacia catechu* | 50 mg |

Embodiments of the disclosed composition in tablet form were analyzed for parameters including physicochemical properties such as Tablet hardness, Loss on drying, Assay, Disintegration time, Ash value, etc and the results were noted. Table 2 depicts the results of the analysis performed to determine the physicochemical properties of an embodiment of the disclosed composition. In an embodiment, the disclosed composition tablets have the characteristics as depicted in Table 2. It will be apparent to those skilled in the levigating Swarna gairika, Khadira rasa and Rasanjana in a grinder;

adding herbs/ingredients and salts into the grinder; and adding grinding decoction while continuing grinding to obtain a ground mass.

The mixture of Swarna gairika, Khadira rasa and Rasanjana may be in semisolid form. In an embodiment, the levigation may be performed for a duration of around 3 hours.

Further, the herbs/ingredients include dried and finely powdered form of heartwood of *Santalum album*, *Prunus cerasoides* and *Aquilaria agallocha*; root of *Vetiveria zizanioides*, *Rubia cordifolia*, *Cyperus rotundus*, *Glycyrrhiza glabra*, *Nardostachys jatamansi* and *Acorus calamus*; flowers of *Woodfordia fruticosa*; flower bud of *Syzygium aromaticum*; stamen of *Messua ferrea*; bark of *Cinnamomum zeylanicum*, *Symplocos racemosus*, *Acacia arabica*, *Ficus benghalensis* and *Ficus glomerata*; seeds of *Elettaria cardamomum* and *Psoralea corylifolia*; rhizome of *Curcuma longa*; root of *Berberis aristata*; plant of *Mimosa pudica*; fruit of *Piper cubeba*, *Emblica officinalis*, *Terminalia chebula* and *Terminalia bellerica*; Lac (Laksha resin) and leaves of *Jasminum officinale*. In an embodiment, finely powdered herbs/herb components may be obtained by powdering and sieving the herb components through 80 mesh screen.

The grinding decoction is a decoction of herbs that may facilitate grinding. In an embodiment, the grinding decoction includes a decoction of at least one herb selected from a list consisting of: *Acacia catechu*, *Acacia arabica*, *Ficus benghalensis*, *Ficus glomerata*, *Sida cordifolia*, *Tinospora cordifolia*, *Plumbago zeylanica*, *Pluchea lanceolata*, *Boerhavia diffusa*, *Terminalia arjuna* and *Embelia ribes*. The decoction may be obtained by any method of decocting generally known in the field. In an embodiment, the method of preparation of grinding decoction further includes, soaking the grinding herbs i.e. water extract of heartwood of *Acacia catechu*, powdered dry bark of *Acacia arabica*, powdered dry bark of *Ficus benghalensis*, powdered dry bark of *Ficus glomerata*, powdered dry root of *Sida cordifolia*, fresh stem of *Tinospora cordifolia*, powdered dry root of *Plumbago zeylanica*, powdered dry root of *Pluchea lanceolata*, powdered dry root of *Boerhavia diffusa*, powdered dry stem bark of *Terminalia arjuna*, and powdered dry fruit of *Embelia ribes*; and concentrating by boiling.

In another embodiment, soaking may be performed by soaking the grinding herbs in 16 parts of water overnight. In a further embodiment, concentrating may be performed by boiling at high temperature, preferably about 80 to 85 degree Celsius, until ⅛th of the liquid remains. Concentration may be confirmed with the help of Brix meter.

Figure 2:
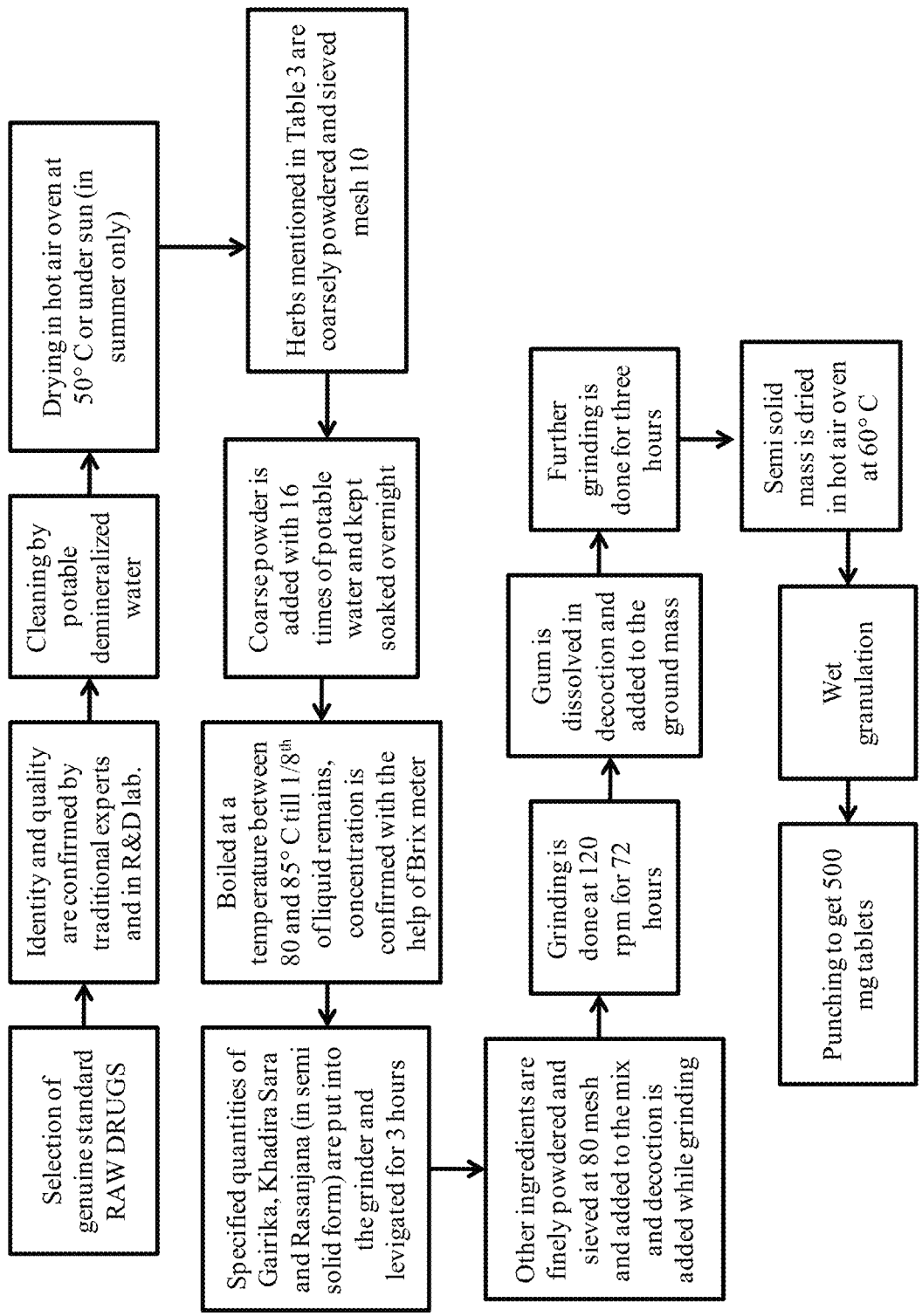
FIG. 2 depicts a flowchart for the preparation of fortified tablets.

Further, once the grinding decoction is added grinding is continued. In an embodiment, grinding is continued for about 72 hours, preferably at 120 rpm, to obtain a ground mass. In an embodiment, the method of preparation may further include adding excipient to the ground mass, wherein gum acacia may be added to the ground mass by dissolving in the grinding decoction while continuing grinding for 3 hours to obtain a semisolid mass. The method of preparation may further include drying at 50 degree Celsius, preferably in a hot air oven, wet granulating, punching to obtain 500 mg tablets. FIG. 2 depicts a flowchart for the preparation of fortified tablets. Table 3 depicts the Herb ingredients required for grinding (grinding herbs) in one of the preferred embodiments.

TABLE 3

| | List of Grinding herbs Decoction of following herbs: | | |
|---|---|---|---|
| 1 | Khadira Sara - water extract of heartwood | Acacia catechu | 1 part |
| 2 | Babbula dry bark | Acacia arabica | 1 part |
| 3 | Vata dry bark | Ficus bengalensis | 1 part |
| 4 | Udumbara dry bark | Ficus glomerata | 1 part |
| 5 | Bala dried root | Sida cordifolia | 1 part |

TABLE 3-continued

| | List of Grinding herbs Decoction of following herbs: | | |
|---|---|---|---|
| 6 | Guduchi fresh stem | Tinospora cordifolia | 1 part |
| 7 | Chitraka dried root | Plumbago zeylanica | 1 part |
| 8 | Rasna dried root | Pluchea lanceolata | 1 part |
| 9 | Punarnava dried root | Boerhavia diffusa | 1 part |
| 10 | Arjuna dried stem bark | Terminalia arjuna | 1 part |
| 11 | Vidanga dried fruit | Embelia ribes | 1 part |
| 12 | Jala | Water | 176 parts |
| | Avashesha (Reduced to) | | ⅛ part of water |

The mineral red ochre used in the various embodiments herein is processed red ochre. It may be processed by any method generally known in the field. In an embodiment, red ochre is processed by levigation using cow's milk, wherein levigation is preferably performed until dryness is achieved and, the process is preferably, repeated seven times. In another embodiment, the levigated red ochre is further dried at about 50° C., powdered and sieved through 80 mesh. FIG. 1(a) illustrates an embodiment of the method of processing red ochre (purification and potentiation of red ochre, also referred to as Swarna gairika Shodhana)

Figure 1B:
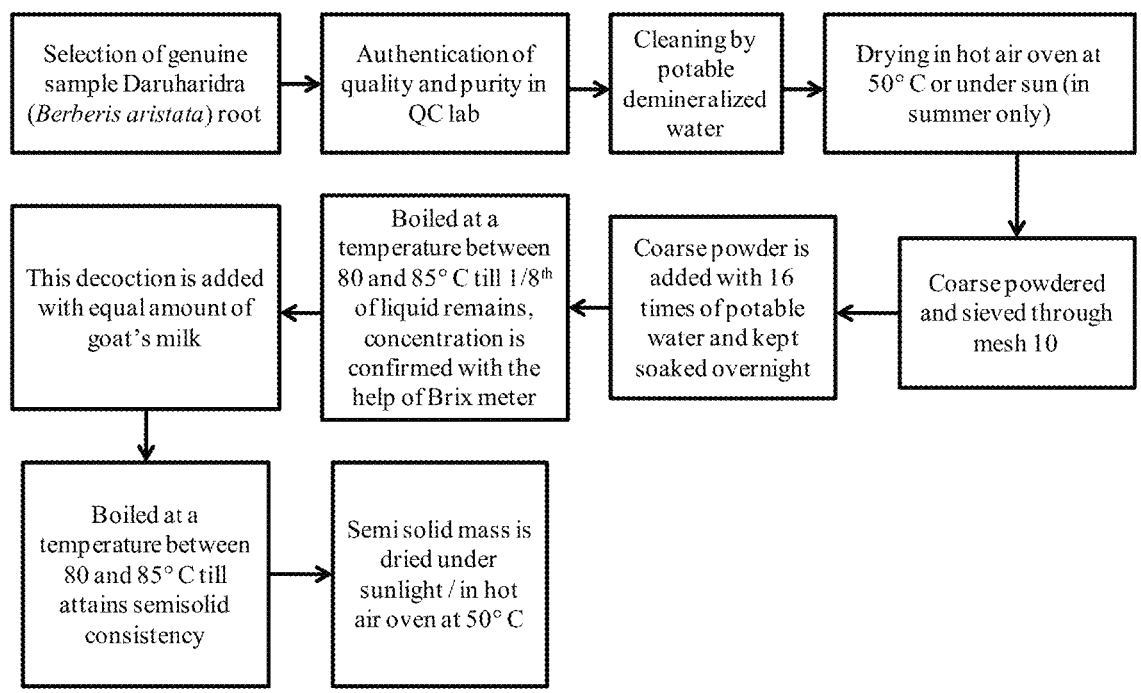
FIG. 1(b) depicts a flowchart for the preparation of Rasanjana.

In an embodiment, Rasanjana includes extract of root of *Berberis aristata*. Rasanjana that is used in the various embodiments herein may be prepared by methods that are generally known in the field. In an embodiment, the method of preparing Rasanjana includes decocting *Berberis aristata* roots, mixing the root decoction with equal amount of goat's milk, concentrating the mixture by boiling at a temperature of about 80 degree C. to 85 degree C. to obtain a semi solid mass. The semisolid mass may further be sun dried or dried in a hot air oven at about 50 degree C. In an embodiment, decocting *Berberis aristata* roots includes drying and coarsely powdering cleaned *Berberis aristata* roots; soaking powdered roots in an amount of 16 times of water, preferably overnight; and concentrating by boiling the mixture at a temperature of about 80° C. to 85° C., preferably until ⅛$^{th}$ of the liquid remains. FIG. 1(b) is a flowchart illustrating a method of preparation of Rasanjana.

Figure 1C:
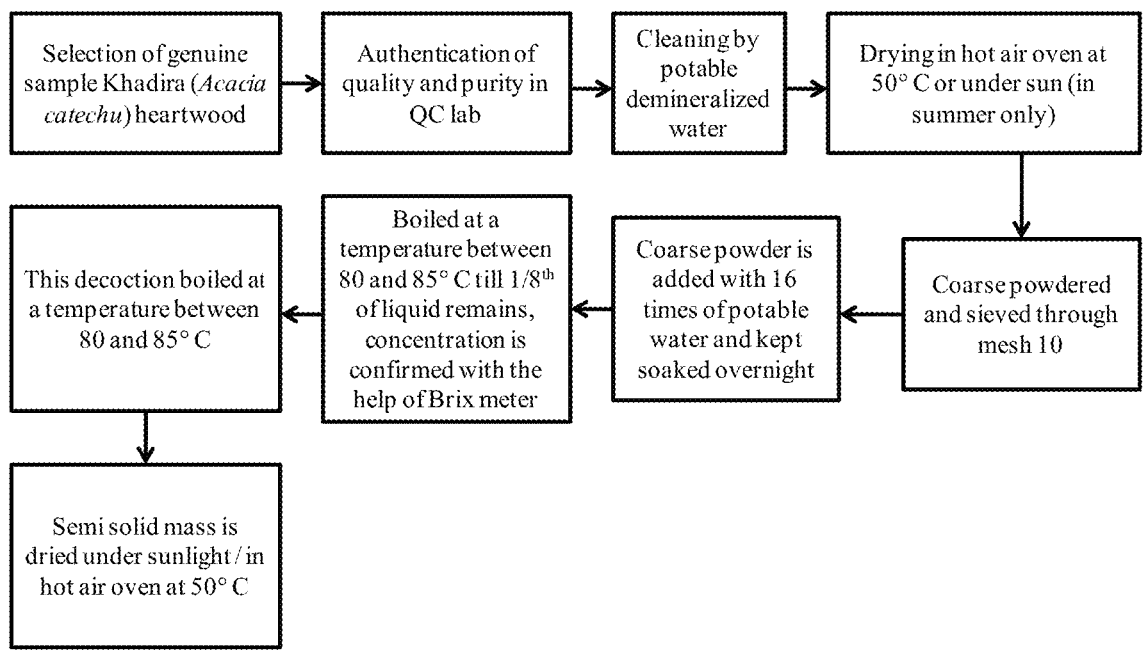
FIG. 1(c) depicts a flowchart for the preparation of Khadira Sara.

In an embodiment, Khadira rasa includes water extract of *Acacia catechu*. Khadira rasa that is used in the various embodiments herein may be prepared by methods that are generally known in the field. In an embodiment, the method of preparing Khadira rasa includes decocting heartwood of *Acacia catechu* and boiling at a temperature of about 80° C. to 85° C. to obtain a semi solid mass. The semisolid mass may further be sun dried or dried in a hot air oven at about 50° C. In an embodiment, decocting heartwood of *Acacia catechu* further includes drying and coarsely powdering cleaned *Acacia catechu* heartwood; soaking powdered roots in an amount of 16 times of water, preferably overnight; and concentrating by boiling the mixture at a temperature of about 80° C. to 85° C., preferably until ⅛$^{th}$ of the liquid remains. FIG. 1(c) is a flowchart illustrating a method of preparation of Khadira rasa.

Treatment

Disclosed herein are embodiments of a method of oral health care. The embodiments disclosed herein are instrumental in improving oral health. Also disclosed are embodiments of a method of treatment and prevention of conditions associated with oral cavity.

In an embodiment, the method includes providing the oral cavity with a therapeutically effective amount of an embodiment of the disclosed oral care composition, wherein the oral care composition includes herb element, mineral element, and suitable excipient, wherein the herb element includes at least one of the following herbs *Santalum album, Prunus cerasoides, Vetiveria zizanioides, Rubia cordifolia, Woodfordia fruticosa, Cyperus rotundus, Glycyrrhiza glabra, Cinnamomum zeylanicum, Elettaria cardamomum, Messua ferrea,* Lac (produced by *Laccifer lacca*), *Nardostachys jatamansi, Symplocos racemosus, Curcuma longa, Berberis aristata, Mimosa pudica, Acorus calamus, Aquilaria agallocha, Syzygium aromaticum, Piper cubeba, Emblica officinalis, Terminalia chebula, Terminalia bellerica, Acacia arabica, Ficus benghalensis, Ficus glomerata, Psoralea corylifolia, Jasminum officinale, Cinnamomum camphor* and *Acacia catechu* or their extracts, or the active ingredients extracted from these herbs; and the mineral element includes at least one of Hematite and rock salt.

The therapeutically effective amount may vary. In an embodiment, the therapeutically effective amount is 500 to 1000 mg provided one or more times a day.

The embodiments of the disclosed oral care composition may be provided to the oral cavity by ways generally known in the field. In an embodiment, providing the oral care composition includes crushing and mixing one or more tablets with few drops of water to form a paste and applying the paste to the oral cavity. The embodiments of the disclosed oral care composition may be applied to the oral cavity with the aid of fingers or brushing appliances such as tooth brush.

In an embodiment, providing the oral care composition includes crushing and mixing one or more tablets with warm water to obtain a suspension; and rinsing the oral cavity with the obtained suspension. For example, two oral care tablets may be crushed and mixed thoroughly with 20 ml of warm water to obtain a suspension which may further be used to rinse the oral cavity.

Embodiments of the disclosed oral care composition (also referred as Test drug) was further tested for efficacy as described hereunder by way of examples. The invention is further described by reference to the following examples by way of illustration only and should not be construed to limit the scope of the present invention. It will be apparent to those skilled in the art that many modifications, both to materials and methods, may be practiced without departing from the scope of the present invention.

Example 1: Experimental Study

The aim of this study was to compare the efficacy of commercially available toothpaste with Test drug on salivary *Streptococcus mutans* count and gingival bleeding index.

Experiment Details:

Subjects: A total of 40 subjects between the age group 9 and 12 years were chosen for our study based on inclusion and exclusion criteria.

Inclusion Criteria:

Systemically healthy controls,

At least, three restored/decayed and/or missing teeth (decayed, missing, and filled teeth [dmft/DMFT]).

Exclusion Criteria:

Subjects who cannot expectorate completely

Subjects who could not brush their teeth on their own

Subjects with a history of taking antibiotics 3 months before and during the study period Subjects undergoing orthodontic treatment or with an intraoral prosthesis Presence of any intra oral pathology Medically compromised subjects.

Method: The subjects were divided into two groups with twenty in each; Group 1 for standard toothpaste and Group 2 for Test drug. The DMFT scores were noted from each subject. Group 1 was instructed to brush with commercially available toothpaste, and Group 2 was instructed to brush using Test drug (herbal). Both the groups brushed teeth using soft variety of tooth brush. The gingival bleeding index and salivary *S. mutans* count were noted pre- and post-brushing for both groups. Each tooth was divided into four parts—disto facial papilla, midfacial papilla, meso facial papilla, entire lingual gingival margin, and scored according to gingival index (Loe and Silness, 1967).

Simplified oral hygiene index: Simplified oral hygiene index (OHI-S) index as described by John C Greene and Jack R Vermillion in 1964 was followed in the study. Instruments used were mouth mirror and explorer. Teeth selected were 16, 11, 26, 36, 31, and 46.

Surface examination: Four posterior and two anterior teeth were selected. The buccal surface of selected upper molar and lingual surface of selected lower molar and incisors were examined.

Criteria followed for classifying debris:

Score 0: No debris or stains

Score 1: Soft debris covering not more than one-third of the tooth surface, or presence of extrinsic stains without other debris regardless of surface area covered Score 2: Soft debris covering more than one-third, but not more than two-third of exposed tooth surface Score 3: Soft debris covering more than one-third of exposed tooth surface.

Criteria followed for classifying calculus:

Score 0: No calculus present

Score 1: Supragingival calculus covering not more than one-third of the exposed tooth surface Score 2: Supragingival calculus covering more than one-third but not more than two-third of the exposed tooth surface or the presence of individual flecks of subgingival calculus around the cervical portion of the tooth or both Score 3: Supragingival calculus covering more than two-third of the exposed tooth surface or the continuous heavy band of subgingival calculus around the cervical portion of the tooth or both.

OHI-S score for each individual was calculated by the debris and calculus scores which were totaled and divided by the number of tooth surfaced scored.

An average of each individual debris and calculus, i.e., simplified debris index (DI-S) and simplified calculus index (CI-S) was scored from range of 0 to 3.

Good: 0.0-0.6

Fair: 0.7-1.8

Poor: 1.9-3.0.

Sum of the DI-S and CI-S will give the OHI-S values ranging from 0 to 6.

Good: 0.0-1.2

Fair: 1.3-3.0

Poor: 3.1-6.0.

The subjects in Group 1 were asked to brush daily with toothpaste which was provided to them. The children in Group 2 were asked to brush with Test drug (herbal) and instructed to crush the tablet and add two drops of water to make it as a paste. Both groups used soft variety of toothbrush to brush the teeth. Both groups were instructed to brush the teeth once daily for 30 days.

A baseline nonstimulated whole salivary sample (2 ml) was collected in the morning by asking the subjects to drool passively into a sterile plastic bottle for 5 min. Subjects were informed not to eat or drink (except water) 1 h before saliva collection to minimize possible contamination from food debris and stimulation of saliva that may interfere in the results of the sample. The samples were collected in sterile bottles and were stored and carried in an ice-containing box (used as transport media). All samples were tested for the number of colony forming units (CFUs) for *S. mutans* using mitis salivarius bacitracin agar.

The gingival bleeding index in Group 1, prebrushing was 1.8050 using toothpaste and Group 2 using Test drug (herbal) was 1.5450 with P value (0.008) showing significance. Table 5 depicts gingival bleeding index in Group 1 and Group 2. The gingival bleeding index postbrushing was 1.6700 for Group 1 and 1.4300 for Group 2 with P value (0.009) showing significance.

TABLE 5

| Group | Gingival bleeding index | Paired differences | | | |
| --- | --- | --- | --- | --- | --- |
| | | Mean | SD | t | p |
| 1 (With toothpaste) | Pre-gingival bleeding index-post gingival bleeding index | 0.13500 | 0.07452 | 8.102 | 0.000 |
| 2 (With test drug) | Pre-gingival bleeding index-post gingival bleeding index | 0.11500 | 0.08751 | 5.877 | 0.000 |

Gingival bleeding index pre and post-rinse with colgate toothpaste and test drug.
SD—Standard Deviation.

Figure 3:
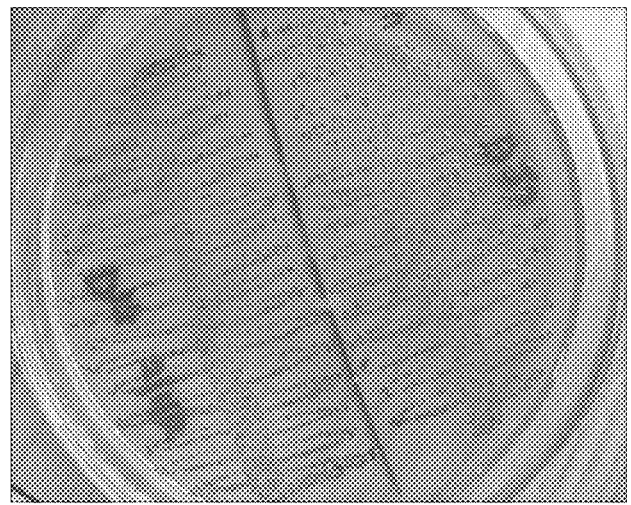
FIG. 3 represents *Streptococcus mutans* on mitis salivaris agar pre-rinse, baseline sample.
Figure 4:
FIG. 4 represents *Streptococcus mutans* on mitis salivaris agar post-rinse using Test drug and toothpaste with toothbrush; according to embodiments as disclosed herein.

Laboratory procedure: The sample was vortexed to get uniform mix of saliva and media using a Cyclo mixer. Vortexed sample was streaked in duplicate on mitis salivarius bacitracin agar selective for *S. mutans* using an inoculation loop (standard loop with 4 mm diameter). The mitis salivarius agar plates were incubated in aerobic conditions for 48 h at 37° C. in an incubator. The plates were opened after 48 h. The counts were made from the colonies with morphologic characteristics of *S. mutans* (0.5 mm raised convex undulated colonies of light blue color with rough margins, granular frosted glass appearance) on the plates using a magnifying lens and were expressed as number of CFU/ml of saliva. Semi quantitation of the number of colonies was done by multiplying the actual colony count with 1×103 as the sample was diluted one thousand times (1:5 dilution). The baseline scores were noted both pre and post rinse. FIG. 2 is an image illustrating *Streptococcus mutans* on mitis salivaris agar pre-rinse, baseline sample. FIG. 3 is an image illustrating *Streptococcus mutans* on mitis salivaris agar post-rinse using Test drug and toothpaste with toothbrush.

Statistical analysis: To assess the gingival bleeding index, paired t-test was used. To assess *S. mutans* count, Mann-Whitney U-test was used.

Results: A total of forty subjects participated in the study. At baseline, Group 1 had a mean *S. mutans* count of 73,800 counts/ml, and Group 2 had 75,608 counts/ml. When Mann-Whitney U-test was performed with the results, the P value was not significant. Hence, it can be inferred that the statistic difference was not significant. Table 4 depicts *Streptococcus mutans* count in Group 1 and Group 2.

TABLE 4

| Group | S. mutans count | Paired differences | | | |
| --- | --- | --- | --- | --- | --- |
| | | Mean | SD | t | p |
| 1 (With toothpaste) | Pre-*S. mutans*-post *S. mutans* | 73,800.0000 | 41,767.02300 | 7.902 | 0.000 |
| 2 (With test drug) | Pre-*S. mutans*-post *S. mutans* | 75,065.0000 | 40,388.23793 | 8.312 | 0.000 |

Salivary Pre-*S. mutans* count pre- and post-rinse with colgate toothpaste and test drug.
SD—Standard Deviation,
Pre-*S. mutans*-*Streptococcus mutans*

Discussion: In this study, both Test drug and toothpaste were found to be useful in effectively reducing the *S. mutans* count and also gingival bleeding index score after usage for 30 days. However, the test drug is considered to be having less or no side effects compared to modern medicine due to the absence of harmful chemicals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. An oral care composition comprising *Prunus cerasoides* in an amount ranging from 2 to 6 wt %, *Glycyrrhiza glabra* in an amount ranging from 6 to 10 wt %, *Berberis aristata* in an amount ranging from 6 to 10 wt %, *Acacia catechu* in an amount ranging from 6 to 10 wt %, *Acacia arabica* in an amount ranging from 6 to 10 wt %, Laksha resin, *Santalum album, Vetiveria zizanioides, Rubia cordifolia, Woodfordia fruticosa, Cyperus rotundus, Cinnamomum zeylanicum, Elettaria cardamomum, Mesua ferrea, Nardostachys jatamansi, Symplocos racemosus, Curcuma longa, Mimosa pudica, Acorus calamus, Aquilaria agallocha, Syzygium aromaticum, Piper cubeba, Emblica officinalis, Terminalia chebula, Terminalia bellerica, Ficus benghalensis, Ficus glomerata, Psoralea corylifolia, Jasminum officinale*, and *Cinnamomum camphor*, wherein:
at least some Laksha resin is present and the at least some Laksha resin is present in an amount of ≤3 wt %,
at least some *Santalum album* is present and the at least some *Santalum album* is present in an amount of ≤2 wt %, at least some *Vetiveria zizanioides* is present and the at least some *Vetiveria zizanioides* is present in an amount of ≤2 wt %, at least some *Rubia cordifolia* is present and the at least some *Rubia cordifolia* is present in an amount of ≤2 wt %, at least some *Woodfordia fruticosa* is present and the at least some *Woodfordia fruticosa* is present in an amount of ≤2 wt %, at least some *Cyperus rotundus* is present and the at least some *Cyperus rotundus* is present in an amount of ≤2 wt %, at least some *Cinnamomum zeylanicum* is present and the at least some *Cinnamomum zeylanicum* is present in an amount of ≤2 wt %, at least some *Elettaria cardamomum* is present and the at least some *Elettaria cardamomum* is present in an amount of ≤2 wt %, at least some *Mesua ferrea* is present and the at least some *Mesua ferrea* is present in an amount of ≤2 wt %, at least some *Nardostachys jatamansi* is present and the at least some *Nardostachys jatamansi* is present in an amount of ≤2 wt %, at least some *Symplocos racemosus* is present and the at least some *Symplocos racemosus* is present in an amount of ≤2 wt %, at least some *Curcuma longa* is present and the at least some *Curcuma longa* is present in an amount of ≤2 wt %, at least some *Mimosa pudica* is present and the at least some *Mimosa pudica* is present in an amount of ≤2 wt %, at least some *Acorus calamus* is present and the at least some *Acorus calamus* is present in an amount of ≤2 wt %, at least some *Aquilaria agallocha* is present and the at least some *Aquilaria agallocha* is present in an amount of ≤2 wt %, at least some *Syzygium aromaticum* is present and the at least some *Syzygium aromaticum* is present in an amount of ≤2 wt %, at least some *Piper cubeba* is present and the at least some *Piper cubeba* is present in an amount of ≤2 wt %, at least some *Emblica officinalis* is present and the at least some *Emblica officinalis* is present in an amount of ≤2 wt %, at least some *Terminalia chebula* is present and the at least some *Terminalia chebula* is present in an amount of ≤2 wt %, at least some *Terminalia bellerica* is present and the at least some *Terminaha bellerica* is present in an amount of ≤2 wt %, at least some *Ficus benghalensis* is present and the at least some *Ficus benghalensis* is present in an amount of ≤2 wt %, at least some *Ficus glomerata* is present and the at least some *Ficus glomerata* is present in an amount of ≤2 wt %, at least some *Psoralea corylifolia* is present and the at least some *Psoralea corylifolia* is present in an amount of ≤2 wt %, at least some *Jasminum officinale* is present and the at least some *Jasminum officinale* is present in an amount of ≤2 wt %, and at least some *Cinnamomum camphor* is present and the at least some *Cinnamomum camphor* is present in an amount of ≤2 wt %; and at least some Hematite is present and the at least some Hematite is present in an amount of ≤3 wt %, of the total composition, wherein said hematite is processed red ochre, and a suitable excipient.

2. The oral care composition as claimed in claim 1, further comprising a salt.

3. The oral care composition as claimed in claim 2, wherein said salt is rock salt.

4. The oral care composition as claimed in claim 2, wherein said salt is present in an amount of ≤3 wt %.

5. The oral care composition as claimed in claim 1, wherein said suitable excipient is gum acacia.

6. The oral care composition as claimed in claim 1, wherein said composition is in a form selected from a group consisting of tablets, pastes, gels, powder, mouth sprays, pellets, lozenges, granules, solutions, emulsions and suspensions.

7. The oral care composition as claimed in claim 1, wherein said composition is in the form of a tablet.

8. The oral care composition as claimed in claim 7, wherein said tablet is in the form of 500 mg tablet.

9. The oral care composition as claimed in claim 1, wherein the composition is a toothpaste, an oral rinse, a tooth whitener, an oral analgesic, an oral antibacterial, a caries prophylactic, an abrasive, or an anti-plaque composition.

10. A process for preparation of the composition claimed in claim 1, comprising:
   levigating Haematite (swarna gairika), Khadira rasa and Rasanjana;
   adding herbs/ingredients and salts, wherein said herbs/ingredients comprises *Santalum album, Aquilaria agallocha, Vetiveria zizanioides, Rubia cordifolia, Cyperus rotundus, Nardostachys jatamansi, Acorus calamus, Woodfordia fruticosa, Syzygium aromaticum, Mesua ferrea, Cinnamomum zeylanicum, Symplocos racemosus, Ficus benghalensis, Ficus glomerata, Elettaria cardamomum, Psoralea corylifolia, Curcuma longa, Cinnamomum camphor, Mimosa pudica, Piper cubeba, Emblica officinalis, Terminalia chebula, Terminalia bellerica*, Laksha resin, and *Jasminum officinale*; and
   adding grinding decoction while continuing grinding to obtain a ground mass.

11. The process as claimed in claim 10, wherein said herbs/ingredients comprises finely powdered form of dry heartwood of *Prunus cerasoides*, dry root of *Glycyrrhiza glabra* and dry bark of *Acacia arabica*.

12. The process as claimed in claim 10, wherein said herbs/ingredients comprises finely powdered form of dry heartwood of *Santalum album* and *Aquilaria agallocha*; dry root of *Vetiveria zizanioides, Rubia cordifolia, Cyperus rotundus, Nardostachys jatamansi* and *Acorus calamus*; dry flowers of *Woodfordia fruticosa*; dry flower bud of *Syzygium aromaticum*; dry stamen of *Mesua ferrea*; dry bark of *Cinnamomum zeylanicum, Symplocos racemosus, Ficus benghalensis* and *Ficus glomerata*; dry seeds of *Elettaria cardamomum* and *Psoralea corylifolia*; dry rhizome of *Curcuma longa*; dry plant of *Mimosa pudica*; dry fruit of *Piper cubeba, Emblica officinalis, Terminalia chebula* and *Terminalia bellerica*; Laksha resin; and dry leaves of *Jasminum officinale*.

13. The process as claimed in claim 10, wherein said salt is rock salt.

14. The process as claimed in claim 10, wherein said grinding decoction is a decoction of at least one selected from the group consisting of heartwood of *Acacia catechu*, bark of *Acacia arabica*, bark of *Ficus benghalensis*, bark of

*Ficus glomerata*, root of *Sida cordifolia*, stem of *Tinospora cordifolia*, root of *Plumbago zeylanica*, root of *Pluchea lanceolata*, root of *Boerhavia diffusa*, stem bark of *Terminalia arjun*, and fruit of *Embelia ribes*.

15. A method of oral health care, said method comprising providing the oral cavity with a therapeutically effective amount of the composition claimed in claim 1.

16. The method of oral health care as claimed in claim 15, wherein said therapeutically effective amount is 500 to 1000 mg.

17. The method of oral health care as claimed in claim 15, wherein providing the oral cavity includes applying the composition to the oral cavity.

18. The method of oral health care as claimed in claim 15, wherein providing the oral cavity includes rinsing the oral cavity with said composition.

19. A method for the treatment and prevention of conditions associated with oral cavity, said method comprising of providing the oral cavity with a therapeutically effective amount of the composition claimed in claim 1.

20. The oral care composition as claimed in claim 1, wherein said composition comprises heartwood of *Prunus cerasoides, Aquilaria agallocha* and *Santalum album*; roots of *Vetiveria zizanioides, Rubia cordifolia, Cyperus rotundus, Glycyrrhiza glabra, Nardostachys jatamansi* and *Acorus calamus*; flowers of *Woodfordia fruticosa*; flower bud of *Syzygium aromaticum*; stamen of *Mesua ferrea*; bark of *Cinnamomum zeylanicum, Symplocos racemosus, Acacia arabica, Ficus benghalensis* and *Ficus glomerata*; seeds of *Elettaria cardamomum* and *Psoralea corylifolia*; rhizome of *Curcuma longa*; root of *Berberis aristata*; plant of *Mimosa pudica*; fruit of *Piper cubeba, Emblica officinalis, Terminalia chebula* and *Terminalia bellerica*; leaves of *Jasminum officinale*; and heartwood of *Acacia catechu*.

\* \* \* \* \*